US008106192B2

(12) United States Patent
Thomas

(10) Patent No.: US 8,106,192 B2
(45) Date of Patent: Jan. 31, 2012

(54) METHOD FOR PRODUCING 5-CHLORO-N-({(5S)-2-OXO-3-[4-(3-OXO-4-MORPHOLINYL)PHENYL]-1,3-OXAZOLIDIN-5-YL}METHYL)-2-THIOPHENECARBOXAMIDE

(75) Inventor: Christian R. Thomas, Wuppertal (DE)

(73) Assignee: Bayer Pharma Aktiengesellschaft, Berlin (DE)

(*) Notice: Subject to any disclaimer, the term of this patent is extended or adjusted under 35 U.S.C. 154(b) by 184 days.

(21) Appl. No.: 12/556,158

(22) Filed: Sep. 9, 2009

(65) Prior Publication Data
US 2010/0081807 A1 Apr. 1, 2010

Related U.S. Application Data

(62) Division of application No. 10/538,342, filed as application No. PCT/EP03/14871 on Dec. 24, 2003, now abandoned.

(30) Foreign Application Priority Data

Jan. 7, 2003 (DE) ................... 103 00 111

(51) Int. Cl.
C07D 413/14 (2006.01)
C07D 333/00 (2006.01)
(52) U.S. Cl. .................. 544/137; 544/146; 549/72
(58) Field of Classification Search ............... 544/137, 544/146; 549/72
See application file for complete search history.

(56) References Cited

U.S. PATENT DOCUMENTS

| 2,811,555 | A | 10/1957 | Larive et al. |
|---|---|---|---|
| 3,279,880 | A | 10/1966 | Straley et al. |
| 4,128,654 | A | 12/1978 | Fugitt et al. |
| 4,250,318 | A | 2/1981 | Dostert et al. |
| 4,327,725 | A | 5/1982 | Cortese et al. |
| 4,500,519 | A | 2/1985 | Lormeau et al. |
| 4,705,779 | A | 11/1987 | Madi-Szabo et al. |
| 4,765,989 | A | 8/1988 | Wong et al. |
| 4,948,801 | A | 8/1990 | Carlson et al. |
| 4,977,173 | A | 12/1990 | Brittelli et al. |
| 5,002,937 | A | 3/1991 | Bosies et al. |
| 5,254,577 | A | 10/1993 | Carlson et al. |
| 5,349,045 | A | 9/1994 | Jiang |
| 5,532,255 | A | 7/1996 | Raddatz et al. |
| 5,561,148 | A | 10/1996 | Gante et al. |
| 5,565,571 | A | 10/1996 | Barbachyn et al. |
| 5,654,428 | A | 8/1997 | Barbachyn et al. |
| 5,654,435 | A | 8/1997 | Barbachyn et al. |
| 5,688,792 | A | 11/1997 | Barbachyn et al. |
| 5,756,732 | A | 5/1998 | Barbachyn et al. |
| 5,792,765 | A | 8/1998 | Riedl et al. |
| 5,801,246 | A | 9/1998 | Barbachyn et al. |
| 5,827,857 | A | 10/1998 | Riedl et al. |
| 5,910,504 | A | 6/1999 | Hutchinson et al. |
| 5,922,708 | A | 7/1999 | Riedl et al. |
| 5,929,248 | A | 7/1999 | Barbachyn et al. |
| 5,935,724 | A | 8/1999 | Spillman et al. |
| 5,972,947 | A | 10/1999 | Tsaklakidis et al. |
| 5,977,373 | A | 11/1999 | Gadwood et al. |
| 5,998,406 | A | 12/1999 | Hester et al. |
| 6,069,160 | A | 5/2000 | Stolle et al. |
| 6,218,413 | B1 | 4/2001 | Hester et al. |
| 6,251,869 | B1 | 6/2001 | Bohanon |
| 6,265,178 | B1 | 7/2001 | Martin, Jr. |
| 6,281,210 | B1 | 8/2001 | Hester, Jr. |
| 6,294,201 | B1 | 9/2001 | Kettelhoit et al. |
| 6,458,793 | B1 | 10/2002 | Warner et al. |
| 6,805,881 | B1 | 10/2004 | Kanikanti et al. |
| 6,818,243 | B2 | 11/2004 | Nagashima et al. |
| 7,034,017 | B2 | 4/2006 | Straub et al. |
| 7,045,631 | B2 | 5/2006 | Rosentreter et al. |
| 7,078,417 | B2 | 7/2006 | Rosentreter et al. |
| 7,109,218 | B2 | 9/2006 | Rosentreter et al. |
| 7,129,255 | B2 | 10/2006 | Rosentreter et al. |
| 7,157,456 | B2 | 1/2007 | Straub et al. |
| 7,351,823 | B2 | 4/2008 | Berwe et al. |
| 2001/0029351 | A1 | 10/2001 | Falotico et al. |
| 2001/0046987 | A1 | 11/2001 | Hester, Jr. et al. |
| 2003/0153610 | A1 | 8/2003 | Straub et al. |
| 2003/0161882 | A1 | 8/2003 | Waterman |
| 2004/0102450 | A1 | 5/2004 | Ewing et al. |
| 2004/0162427 | A1 | 8/2004 | Rosentreter et al. |
| 2004/0242660 | A1 | 12/2004 | Straub et al. |
| 2005/0064006 | A1 | 3/2005 | Perzborn et al. |
| 2005/0182055 | A1 | 8/2005 | Berwe et al. |
| 2005/0261502 | A1 | 11/2005 | Rosentreter et al. |
| 2006/0154969 | A1 | 7/2006 | Rosentreter et al. |

(Continued)

FOREIGN PATENT DOCUMENTS

AU 744002 2/2002

(Continued)

OTHER PUBLICATIONS

[Database Bielstein] Beilstein Institute for Organic Chemistry, Frankfurt-Main, DE. Database Accession No. 8822985.
Bono, F., et al., "Human Umbilical Vein Endothelial Cells Express High Affinity Receptors for Factor Xa", Journal of Cellular Physiology, 1997, vol. 172, pp. 36-43.
Cocks, T. M., et al., "Protease-Activated Receptors: Sentries for Inflammation", Tips, 2000, vol. 21, pp. 103-108.
Ross, R., "Atherosclerosis—An Inflammatory Disease", New England J. of Medicine, 1999, vol. 340, No. 2, pp. 115-126.
Nakata, M., et al., "DX9065a an Xa Inhibitor, Inhibits Prothrombin-Induced A549 Lung Adenocarcinoma Cell Proliferation", Cancer Letters, 1998, vol. 122, pp. 127-133.
Kaiser, B., et al., "A Synthetic Inhibitor of Factor Xa, DX-9065a, Reduces Proliferation of Vascular Smooth Muscle Cells In Vivo in Rats", Thrombosis Research, 2000, vol. 98, pp. 175-185.

(Continued)

Primary Examiner — Rebecca Anderson
Assistant Examiner — Samantha Shterengarts
(74) Attorney, Agent, or Firm — Connolly Bove Lodge & Hutz, LLP

(57) ABSTRACT

The invention relates to a method for producing 5-chloro-N-({5S}-2-oxo-3-[4-(3-oxo-4-morpholinyl)-phenyl]-1,3-oxazolidin-5-yl}-methyl)-2-thiophenecarboxamide starting from 5-chlorothiophene-2-carbonyl chloride, (2S)-3-aminopropane-1,2-diol and 4-(4-aminophenyl)-3-morpholinone.

9 Claims, No Drawings

U.S. PATENT DOCUMENTS

| | | |
|---|---|---|
| 2006/0258724 A1 | 11/2006 | Straub et al. |
| 2007/0026065 A1 | 2/2007 | Benke et al. |
| 2007/0149522 A1 | 6/2007 | Thomas |
| 2008/0026057 A1 | 1/2008 | Benke |
| 2008/0090815 A1 | 4/2008 | Straub et al. |
| 2008/0200674 A1 | 8/2008 | Straub et al. |

FOREIGN PATENT DOCUMENTS

| | | |
|---|---|---|
| DE | 28363051 A1 | 3/1979 |
| DE | 196 04 223 | 8/1997 |
| DE | 19962924 A1 | 7/2001 |
| DE | 10105989 A1 | 8/2002 |
| DE | 10129725 A1 | 1/2003 |
| DE | 10355461 A1 | 6/2005 |
| EP | 0 127 902 | 12/1984 |
| EP | 0 316 594 | 5/1989 |
| EP | 0 352 781 | 1/1990 |
| EP | 0350002 A1 | 1/1990 |
| EP | 0 623 615 | 11/1994 |
| EP | 0645376 | 3/1995 |
| EP | 0 738 726 | 10/1996 |
| EP | 0 785 200 | 7/1997 |
| EP | 0930076 A1 | 7/1999 |
| EP | 0950386 A2 | 10/1999 |
| GB | 2140687 | 12/1984 |
| WO | WO-93/09103 | 5/1993 |
| WO | WO-93/23384 | 11/1993 |
| WO | WO-97/03072 | 1/1997 |
| WO | WO-97/09328 | 3/1997 |
| WO | WO-97/10223 | 3/1997 |
| WO | WO-98/01446 | 1/1998 |
| WO | WO-98/54161 | 12/1998 |
| WO | WO-99/02525 | 1/1999 |
| WO | WO-99/03846 | 1/1999 |
| WO | WO-99/06371 | 2/1999 |
| WO | WO-99/21535 A1 | 5/1999 |
| WO | WO-99/24428 | 5/1999 |
| WO | WO-99/29688 | 6/1999 |
| WO | WO-99/31092 | 6/1999 |
| WO | WO-99/37304 | 7/1999 |
| WO | WO-99/37630 | 7/1999 |
| WO | WO-99/37641 | 7/1999 |
| WO | WO-99/40094 | 8/1999 |
| WO | WO-99/59616 | 11/1999 |
| WO | WO-00/16748 A1 | 3/2000 |
| WO | 0147919 | 5/2001 |
| WO | WO-01/44212 A1 | 6/2001 |
| WO | WO-01/46185 A1 | 6/2001 |
| WO | WO-01/47949 A1 | 7/2001 |
| WO | WO-02/25210 A1 | 3/2002 |
| WO | WO-02/064575 A1 | 8/2002 |
| WO | WO-02/070484 A1 | 9/2002 |
| WO | WO-02/070485 A1 | 9/2002 |
| WO | WO-02/070520 A1 | 9/2002 |
| WO | WO-02/079195 A1 | 10/2002 |
| WO | WO-02/079196 A1 | 10/2002 |
| WO | WO-03/008384 A1 | 1/2003 |
| WO | 03000256 | 3/2003 |
| WO | WO-03/035133 A1 | 5/2003 |
| WO | WO-03/053441 A1 | 7/2003 |
| WO | WO-2004/060887 A1 | 7/2004 |
| WO | WO-2005/060940 A1 | 5/2005 |
| WO | WO-2005/068456 A1 | 7/2005 |
| WO | WO-2006/072367 A1 | 7/2006 |
| WO | WO-2006/079474 A1 | 8/2006 |
| WO | WO-2007/036306 A1 | 4/2007 |
| WO | WO-2007/039122 A2 | 4/2007 |
| WO | WO-2007/039132 A1 | 4/2007 |
| WO | WO-2007/039134 A1 | 4/2007 |
| WO | WO-2007/042146 A1 | 4/2007 |
| WO | WO-2008/012002 A1 | 1/2008 |
| WO | WO-2008/052671 A1 | 5/2008 |

OTHER PUBLICATIONS

Altieri, D. C., et al, "Identification of Effector Cell Protease Receptor-1", The Journal of Immunology, 1990, vol. 145, No. 1, pp. 246-253.

Coughlin, S. R., "Thrombin Signalling and Protease-Activated Receptors", Nature, 2000, vol. 407, pp. 258-264.

Ornstein, D. L., et al., "Cancer, Thrombosis, and Anticoagulants", Current Opinion in Pulmonary Medicine, 2000, vol. 6, pp. 301-308.

Dabbagh, K., et al., "Thrombin Stimulates Smooth Muscle Cell Procollagen Synthesis and mRNA Levels via a PAR-1 Mediated Mechanism", Thrombosis and Haemostasis, vol. 79, No. 2 1997, pp. 405-409.

Herault, J-P., et al., "Activation of Human Vascular Endothelial Cells by Factor Xa: Effect of Specific Inhibitors", Biochemical Pharmacology, 1999, vol. 57, pp. 603-610.

Leveugle, B., et al., "Heparin Oligosaccharides that Pass the Blood-Brain Barrier Inhibit β-Amyloid Precursor Protein Secretion and Heparin Binding to β-Amyloid Peptide", Journal of Neurochemistry, 1998, vol. 70, No. 2, pp. 736-744.

Molino, M., et al., "Differential Expression of Functional Protease-Activated Receptor-2 (PAR-2) in Human Vascular Smooth Muscle Cells", Arteriosclerosis, Thrombosis, and Vascular Biology, vol. 18, No. 5, 1998, pp. 825-832.

Plescia, J., et al., "Activation of MAC-1 (CD11b/CD18)-Bound Factor X by Release Cathepsin G Defines an Alternative Pathway of Leucocyte Initiation of Coagulation", Biochem. J., 1996, vol. 319, pp. 873-879.

Howells, G. L., et al., "Proteinase-Activated Receptor-2: Expression by Human Neutrophils", Journal of Cell Science, 1997, vol. 110, pp. 881-887.

Herbert, J.-M., et al, "Effector Protease Receptor 1 Mediates the Mitogenic Activity of Factor Xa for Vascular Smooth Muscle Cells In Vitro and In Vivo", J. Clin. Invest., 1998, vol. 101, No. 5, pp. 993-1000.

Donnelly, K. M., et al., "*Ancylostoma caninum* Anticoagulant Peptide Blocks Metastasis In Vivo and Inhibits Factor Xa Binding to Melanoma Cells In Vitro", Thromb Haemost, 1998, vol. 79, pp. 1041-1047.

Ragosta, M., et al., "Specific Factor Xa Inhibition Reduces Restenosis After Balloon Angioplasty of Atherosclerotic Femoral Arteries in Rabbits", Circulation, 1994, vol. 89, No. 3, pp. 1262-1271.

Zhang, Y., et al., "Tissue Factor Controls the Balance of Angiogenic and Antiangiogenic Properties of Tumor Cells in Mice", J. Clin. Invest., 1994, vol. 94, pp. 1320-1327.

Green, D., et al., "Lower Mortality in Cancer Patients Treated with Low-Molecular-Weight Versus Standard Heparin", The Lancet, 1992, vol. 339, p. 1476.

Ko, F. N., et al., "Coagulation Factor Xa Stimulates Platelet-Derived Growth Factor Release and Mitogenesis in Cultured Vascular Smooth Muscle Cells of Rat", J. Clin. Invest., 1996, vol. 98, No. 6, pp. 1493-1501.

Kakkar, A. K., et al., "Antithrombotic Therapy in Cancer", BMJ, 1999, vol. 3318, pp. 1571-1572.

Gasic, G. P., et al., "Coagulation Factors X, Xa, and Protein S as Potent Mitogens of Cultured Aortic Smooth Muscle Cells", Proc. Natl. Acad. Sci. USA, 1992, vol. 89, pp. 2317-2320.

Cirino, G., et al., "Factor Xa as an Interface Between Coagulation and Inflammation: Molecular Mimicry of Factor Xa Association with Effector Cell Protease Receptor-1 Induces Acute Inflammation In Vivo", J. Clin. Invest., 1997, vol. 99, No. 10, pp. 2446-2451.

Senden, N. H. M., et al., "Factor Xa Induces Cytokine Production and Expression of Adhesion Molecules by Human Umbilical Vein Endothelial Cells", The Journal of Immunology, 1998, vol. 161, pp. 4318-4324.

Papapetropoulos, A., et al., "Hypotension and Inflammatory Cytokine Gene Expression Triggered by Factor Xa-Nitric Oxide Signaling", Proc. Natl. Acad. Sci. USA, 1998, vol. 95, pp. 4738-4742.

Camerer, E., et al., "Tissue Factor- and Factor X-dependent Activation of Protease-Activated Receptor 2 by Factor VIIa", PNAS, 2000, vol. 97, No. 10, pp. 5255-5260.

Donovan, F. M., et al., "Thrombin Induces Apoptosis in Cultured Neurons and Astrocytes via a Pathway Requiring Tyrosine Kinase and RhaA Activities", The Journal of Neuroscience, 1997, vol. 17, No. 14, pp. 5316-5326.

Lindner, J. R., et al., "Delayed Onset of Inflammation in Protease-Activated Receptor-2-Deficient Mice", The Journal of Immunology, 2000, pp. 6504-6510.

Bouchard, B. A., et al., "Effector Cell Protease Receptor-1, a Platelet Activation-dependent Membrane Protein, Regulates Prothrombinase-catalyzed Thrombin Generation", The Journal of Biological Chemistry, 1997, vol. 272, No. 14, pp. 9244-9251.

Molino, M., et al., "Endothelial Cell Thrombin Receptors and PAR-2", The Journal of Biological Chemistry, 1997, vol. 272, No. 17, pp. 11133-11141.

Nicholson, A. C., et al., "Effector Cell Protease Receptor-1 Is a Vascular Receptor for Coagulation Factor Xa", The Journal of Biological Chemistry, 1996, vol. 271, No. 45, pp. 28407-28413.

Watson, D. J., et al., "Heparin-Binding Properties of the Amyloidogenic Peptides Aβ and Amylin", The Journal of Biological Chemistry, 1997, vol. 272, No. 50, pp. 31617-31624.

Tuszynski, G. P., et al., "Isolation and Characterization of Antistasin", The Journal of Biological Chemistry, 1987, vol. 262, No. 20, pp. 9718-9723.

Kranzhöfer, R., et al., "Thrombin Potently Stimulates Cytokine Production in Human Vascular Smooth Muscle Cells but Not in Mononuclear Phagocytes", Circulation Research, 1996, vol. 79, No. 2, pp. 286-294.

Schwartz, R. S., et al., "Neointimal Thickening After Severe Coronary Artery Injury is Limited by Short-term Administration of a Factor Xa Inhibitor", Circulation, 1996, vol. 93, No. 8, pp. 1542-1548.

Abendschein, D. R., et al., "Inhibition of Thrombin Attenuates Stenosis After Arterial Injury in Minipigs", JACC, 1996, vol. 28, No. 7, pp. 1849-1855.

Carmeliet, P., et al., "Gene Manipulation and Transfer of the Plasinogen and Coagulation System in Mice", Seminars in Thrombosis and Hemostasis, 1996, vol. 22, No. 6, pp. 525-542.

Stouffer, G. A., et al., "The Role of Secondary Growth Factor Production in Thrombin-Induced Proliferation of Vascular Smooth Muscle Cells", Seminars in Thrombosis and Hemostasls, 1998, vol. 24, No. 2, pp. 145-150.

Bevilacqua, M. P., et al., "Inducible Endothelial Functions in Inflammation and Coagulation", Seminars in Thrombosis and Hemostasis, 1987, vol. 13, No. 4, pp. 425-433.

Riedl, B., et al., "Recent Developments with Oxazolidinone Antibiotics", Exp. Opin. Ther. Patents, 1999, vol. 9, No. 5, pp. 625-633.

Barbachyn, M.R., et al., "Identification of Novel Oxazolidinone (U-100480) with Potent Antimycobacterial Activity", J. Med. Chem., 1996, vol. 39, pp. 680-685.

Tucker, J. A., et al, "Piperazinyl Oxazolidinone Antibacterial Agents Containing a Pyridine, Diazene, or Triazene Heteroaromatic Ring", J. Med. Chem. 1998, vol. 41, pp. 3727-3735.

Brickner, S.J., et al., "Synthesis and Antibacterial Activity of U-100592 and U-100766, Two Oxazolidinone Antibacterial Agents for the Potenial treatment of Multidrug-Resistant Gram-Positive Bacterial Infections" J. Med. Chem., 1996, vol. 39, pp. 673-679.

Gregory, W.A., et al., "Antibacterials. Synthesis and Structure-Activity Studies of 3-Aryl-2-oxooxazolidines. 1. The "B" Group", J. Med. Chem., 1989, vol. 32, No. 8, pp. 1673-1681.

Berry, C. N., et al., "Antithrombotic Actions of Argatroban in Rat Models of Venous, 'Mixed' and Arterial Thrombosis, and its Effects on the Tail Transection Bleeding Time", Br. J. Pharmacol., 1994, vol. 113, pp. 1209-1214.

Meng, K., et al., "Effect of Acetylsalicyclic Acid of Experimentally Induced Arterial Thrombosis in Rats", Naunyn-Schmiedeberg's Arch. Pharmacol.,1977, vol. 301, pp. 115-119.

Chern, J.W., et al., "Studies on Quinazolines IX:[1] Fluorination Versus 1,2-Migration on the Reaction of 1,3-Bifunctionalized Amino-2-Propanol with DAST", Tetrahedron Lett., 1998, vol. 39, pp. 8483-8486.

Shakespeare, W. C., et al., "Palladium-Catalyzed Coupling of Lactams with Bromobenzenes", Tetrahedron Lett., 1999, vol. 40, pp. 2035*2038.

Renger, B., et al., "Direkte N-Arylierung von Amiden: Eine Verbesserung der Goldberg-Reaktion", Synthesis, 1985, pp. 856-860.

Aebischer, E., et al., "Synthesis of N-Arylrolipram Derivatives—Potent and Selective Phosphodiesterase-IV Inhibitors—by Copper Catalyzed Lactam-Aryl Halide Coupling", Hetercycles, 1998, vol. 48, No. 11, pp. 2225-2229.

Pfeil, E., et al., "β-Aminoäthylierung von Indol und 2-methylindol", Angew Chem., 1967, vol. 79, No. 4, pp. 188-189.

Ziegler, C. B., et al., "Synthesis of Some Novel 7-Substituted Quinolonecarboxylic Acids via Nitroso and Nitrone Cycloadditions", J. Hetercycl. Chem., 1988, vol. 25, No. 2, pp. 719-723.

Bartoli, G., et al, "Electronic and Steric Effects in Nucleophilic Aromatic Substitution. Reaction by Phenoxides as Nucleophiles in Dimethyl Suifoxide", J. Org. Chem., 1975, vol. 40, No. 7, pp. 872-874.

Reppe, et al., "N-p-Merthoxyphenyl-pyrrolidon", Justus Liebigs Ann. Chem., 1955 vol. 596, p. 208.

Luvalle, J.E., et al., "Oxidation Processes. XXI.[1] The Autoxidation of the ρ-Phenylenediamines", J. kn. Chem. Soc., 1948, vol. 70, pp. 2223-2233.

Snyder, H.R., et al., "Imidazo[4,5 f]quinolines III: Antibacterial 7-Methyl-9-(substituted Arylamino)imidazo[4,5-f]quinolines", J. Pharm. Sci., 1977, vol. 66, pp. 1204-1406.

Adams, R., et al., "Sulfanilamide Derivatives. I", J. Am. Chem. Soc. 1939, vol. 61, pp. 2342-2349.

Khanna, I.K., et al., "1,2-Diarylpyrrotes as Potent and Selective Inhibitors of Cyclooxygenase-2", J. Med. Chem., 1997, vol. 40 , pp. 1619-1633.

Gutcait, A., et al., "Studies on Quinazolines. 6.[1] Asymmetric Synthesis of (S)-(+)- and (R)-(-)-3-[[4-(2-Methoxyphenyl)piperazin-1-yl]methylthio-2,3,-dihydrornidazo[1,2-c]quinazolines", Tetrahedron Asym., 1996, vol. 7, No. 6, pp. 1641-1648.

Grell, W., et al., "Repaglinide and Related Hypoglycemic Benzoic Acid Derivatives", J. Med. Chem., 1998, vol. 41, pp. 5219-5246.

Artico, M. et al., "Rsearch on Compounds with Antiblastic Activity", Farmaco Ed. Sci. 1969, vol. 24, pp. 179-190.

Dankwardt, S. M., et al., "Nonpeptide Bradykinin Antagonist Analogs based on a Model of a Sterling-Winthrop Nonpeptide Bradykinin Antagonist Overlapped with Cyclic Hexapeptide Bradykinin Antagonist Peptides", Bioorg. Med. Chem. Lett., 1997, vol. 7, No. 14, pp. 1921-1926.

Reppe, et al., "N-6-Aminohexyl-pyrrolidon", Justus Liebigs Ann. Chem. 1955, vol. 596, pp. 204.

Bouchet, P., et al., "σ Values of N-Substitutes Azoles", J. Chem. Soc. Perkin Trans., 1974, vol. 2, pp. 449-451.

Surrey, A. R., et al., "The Preparation of N-Benzyl-3-Morpholones and N-Benzyl-3-Homomorpholones from N-(Hydroxyalkyl)-chloroacetamides" J. Amer. Chem. Soc., 1955, vol. 77, pp. 633-636.

Tong, L.K.J., et al., "The Mechanism of Dye Formation in Color Photography. VII. Intermediate Bases in the Deamination of Quinonedilmines" J. Amer. Chem. Soc. 1960, vol. 82, 1988-2001.

Delande, S.A., "Heterocycles", Chemical Abstracts, American Chemical Society, 1979, vol. 90, pp. 663.

Bots, M., et al., Coagulation and Fibrinolysis Markers and Risk of Dementia, Haemostasis, vol. 28 (1998); pp. 216-222.

Benzakour, O., et al., "Cellular and molecular events in atherogenesis; basis for pharmacological and gene therapy approaches to stenosis," Cellular Pharmacology, 1996, vol. 3, pp. 7-22.

Kanthou, C., et al., "Cellular effects of thrombin and their signalling pathways," Cellular Pharmacology, vol. 2 (1995); pp. 293-302.

Kaiser, B., et al., "Antiproliferation Action of Factor Xa Inhibitors in a Rat Model of Chronic Restenosis," Abstracts of the XVIIth Congress of the International Society on Thrombosis and Haemostasis, Aug. 1999, p. 144.

Tyrrell, D., et al., "Heparin in Inflammation: Potential Therapeutic Applications Beyond Anticoagulation," Advances in Pharmacology, vol. 46 (1999); pp. 151-208.

Smirova, I., et al., "Thrombin Is an Extracellular Signal that Activates Intracellular Death Protease Pathways Inducing Apoptosis in Model Motor Neurons," J. Neurobiology, vol. 36 (1998); pp. 64-80.

Bono, F., et al., "Factor Xa Activates Endothelial Cells by a Receptor Cascade Between EPR-1 and PAR-2," Arterloscler Thromb Vasc Biol., Nov. 2000; pp. 1-6.

Lala, P. et al, "Role of Nitric Oxide in tumor progression: Lessons Learned from Experimental Tumors," Cancer and Metastasis Review, vol. 17, pp. 91-108 (1998).

Golub, T., et al., Molecular Classification of Cancer Science (1999), vol. 286, 531-537.

FDA mulls drug to slow late-stage Azheimers [online], [retrieved on Sep. 23, 2003]. Retrieved from the internet, URL:http://www.cnn.com/2003/HEALTH/conditions/09/24/alzheimers.drug.ap/index.html>.

Ulllman's Encyclopedia of Industrial Chemistry, Fifth Revised Ed., Editors: Elvers, B., Hawkins, S., VCH Verlagsgesellschaft mbH, Weinheim, 19985-1996, Ch. 5, 488-506.

Zhu, B., Scarborough, R., "Recent Advances in Inhibitors of Factor Xa in the Prothrombinase Complex," *Curr. Opinions Card. Pul. Ren. Inv. Drugs*, 1:63-87 (1999).

Uzan, A., "Antithrombotic Agents," *Emerging Drugs: The Prospect for Improved Medicines*, 3: 189-208 (1998).

Kaiser, B., "Thrombin and Factor Xa Inhibitors," *Drugs of the Future*, 23: 423-426 (1998).

Al-Obeidi, F., Ostrem, J., "Factor Xa Inhibitors," *Expert Opin. Therapeutic Patents*, 9: 931-953 (1999).

Al-Obeidi, F., Ostrem, J., "Factor Xa Inhibitors by Classical and Combinatorial Chemistry," *DDT*, 3: 223-231 (May 1998).

Hauptmann, J.,et al., "Synthetic Inhibitors of Thrombin and Factor Xa: From Bench to Bedside," *Thrombosis Research*, 93: 203-241 (1999).

Pschyrembel, Klinisches Worterbuch, 257. Auflage, 1994, Walter de Gruyter Verlag, p. 199-200, Stichwort "Blutgerinnung."

Rompp Lexikon Chemie, Ver. 1.5, 1998, Georg Thieme Verlag Stuttgart, Stichwort "Blutgerrinung" Lubert Stryer, Biochemie, Spektrum der Wissenschaft Verlagsgesellschaft mbH Heidelberg, 1990, p. 259.

Pschyrembel, Klinisches Worterbuch, 257. Auflage, 1994, Walter de Gruyter Verlag, p. 610, Stichwort "Heparin."

Rompp Lexikon Chemie, Ver. 1.5, 1998, Georg Thieme Verlag Stuttgart, Stichwort "Heparin."

Pschyrembel, Klinisches Worterbuch, 257. Auflage, 1994, Walter de Gruyter Verlag, p. 292, Stichwort "Cumarinderivate."

Becker, M.R., et al., "Synthesis, Sar and in Vivo Activity of Novel Thienopyridine Sulfonamide Pyrrolidininones as Factor Ka Inhibitors," *Bioorganic and Medicinal Chemistry Letters*, 9: 2753-2758 (1999).

Linder, J., et al., "Delayed Onset of Inflammation in Protease-Activated Receptor-2-Deficient Mice," J. Immunology, 2000, pp. 6504-6510.

Cirino, G. et al. Inflammation-Coagulation Network: Are Serine Protease receptors the knot?; Tips; 200, vol. 21, pp. 170-172.

Roehrig, S. et al. Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor. J. Med. Chem. 48, 22. Sep. 2005, pp. 5900-5908.

Caira, M. Crystalline Polymorphism of Organic Compounds. Springer Verlag Berlin Heidelberg 198, 1998, pp. 163-208.

Hancock, B. et al. Characteristics and Significance of the Amorphous State in Pharmaceutical Systems. Journal of Pharmaceutical Science. 86, 1 (Jan. 1997), pp. 1-12.

Chiou, W.L. et al. Pharmaceutical Applications of Solid Dispersion Systems. Journal of Pharmaceutical Sciences 60, (1971). 128-1302.

Ford, J.L. The Current Status of Solid Dispersions. Pharrn Acta Helv. 61, (1986)69-88.

Rasenack, N. et al. Poorly Water-soluble Drugs for Oral Delivery—A Challenge for Pharmaceutical Development. Pharmazeutische Industrie 67, Nr. 5 (2005), 583-591.

Breitenbach, J. Melt extrusion: from process to drug delivery technology. European Journal of Pharmaceutics and Biopharmaceutics 54 (2002) 107-117.

Breitenbach, J. Feste Loesungen durch Schmelzextrusion—ein integriertes Herstellkonzept. Pharmazie in unserer Zeit 29 (2000), 46-49.

http://familydoctor.org/online/famdocen/home/common/heartdisease/basics/290.html.

Kubitza, et al., Multiple dose escalation study Investigating the pharmacodyanamics, safety, and pharmacokinetics of BAY 59-7939 an oral, direct Factor Xa inhibitor in healthy male subjects, Blood, vol. 102:11:Nov. 16, 2003, p. 811a.

Kubitza, et al., Abstract 3010, Single dose escalation study investigating the pharmacodyanamics, safety, and pharmacokinetics of Bay 59-7939 an oral, direct Factor Xa inhibitor in healthy male subjects, Blood, vol. 102:11. Nov. 16, 2003, p. 813a.

Lerk, et al., Effect of Hydrophilization Drugs on Release Rat from Capsules, J. of Pharma. Sciences, 67(7), pp. 935-939 (1978).

Lerk, et al., In Vitro and In Vivo Availability of Hydrophillzed Phenytoin from Capsules, J. of Pharma. Sciences, 68(5), pp. 634-638 (1979).

Greaves, et al., Novel Approaches to the Preparation of Low-Dose Solid Dosage Forms,Pharmaceutical Technology. January, pp. 60-64, (1995).

Gilligan, D.M. et al. The Management of Atrial Fibrillation. The American Journal of Medicine, vol. 101, (4) 1996, 413-421.

Kubitza, D. et al. Novel factor Xa inhibitors for prevention and treatment of thromboembolic diseases. Expert Opinion on Investig. Drugs, vol. 15, (8) 2006, pp. 843-855.

Sinha, U. et al. Antithrombotic and hemostatic capacity of factor Xa versus thrombin inhibitors in models of venous and arteriovenous thrombosis. European Journal of Pharmacology 2000, 395, 51-59.

Betz, A. Recent advances in Factor Xa inhibitors, Expert Opinion Ther. Patents 2001, 11(6), 1007-1017.

Tan, K.T. et al. Factor X inhibitors. Expert Opinion on Investig. Drugs 2003,12, 799-804.

Ruef, J. et al. New antithrombotic drugs on the horizon. Expert Opinion on Investig. Drugs 2003, 12, 781-797.

Samama, M.M. Synthetic direct and indirect factor Xa inhibitors. Thrombosis Research 2002, 106, V267-V273.

Quan, M.L. The race to an orally active Factor Xa inhibitor: Recent advances. Current Opinion in Drug Discovery & Development 2004, 7, 460-469.

The Ephesus Study, Blood 2000, 96, 490a.

The Penthifra Study, Blood 2000, 96, 490a.

The Pentamaks Study, Blood 2000, 96, 490a-491a.

Leadley, R.J. Coagulation Factor Xa Inhibition: Biological Background and Rationale. Current Topics in Medicinal Chemistry 2001, 1, 151-159.

The Penthathlon 2000 Study, Blood 2000, 96, 491a.

Williams, E.M. Vaughan. Classificating anti-arrhythimic drugs. In: Cardiac Arrythias—Proceedings of a symposium, sandoe E., soedertaeje: Astra (1970), pp. 449-469.

Reppe, et al., Justus Liebigs Ann. Chem. 596, 1955, p. 209.

[Database Bielstein] Bielstein Institute for Organic Chemistry, Frankfurt-Main, DE. Database Accession No. 8822985.

METHOD FOR PRODUCING 5-CHLORO-N-({(5S)-2-OXO-3-[4-(3-OXO-4-MORPHOLINYL)PHENYL]-1,3-OXAZOLIDIN-5-YL}METHYL)-2-THIOPHENECARBOXAMIDE

This application is a divisional application of U.S. application Ser. No. 10/538,342 filed Jun. 5, 2006, now abandoned which is hereby incorporated by reference herein in its entirety, and further which is a national stage application (under 35 U.S.C. 371) of PCT/EP03/14871 filed Dec. 24, 2003, which claims benefit of German application 103 00 111.5 filed Jan. 7, 2003.

The present invention relates to a process for preparing 5-chloro-N-({(5S)-2-oxo-3-[4-(3-oxo-4-morpholinyl)phenyl]-1,3-oxazolidin-5-yl}methyl)-2-thiophene-carboxamide starting from 5-chlorothiophene-2-carbonyl chloride, (2S)-3-aminopropane-1,2-diol and 4-(4-aminophenyl)-3-morpholinone.

The compound 5-chloro-N-({(5S)-2-oxo-3-[4-(3-oxo-4-morpholinyl)phenyl]-1,3-oxazolidin-5-yl}methyl)-2-thiophenecarboxamide is known from WO-A 01/47919 and corresponds to the formula (I)

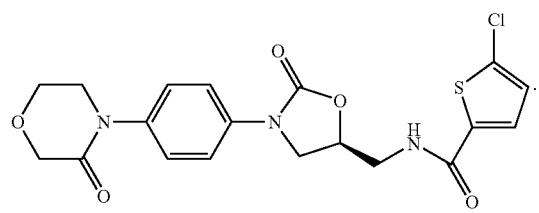

(I)

The compound of the formula (I) acts as an inhibitor of clotting factor Xa and may be used as an agent for the prophylaxis and/or treatment of thromboembolic disorders, especially myocardial infarction, angina pectoris (including unstable angina), reocclusions and restenoses after angioplasty or aortocoronary bypass, stroke, transient ischemic attacks, peripheral arterial occlusive diseases, pulmonary embolisms or deep venous thromboses.

WO-A 01/47919 also describes a method for preparing the compound of the formula (I) starting from 2-[(2S)-2-oxiranylmethyl]-1H-isoindole-1,3(2H)-dione (II), 4-(4-aminophenyl)-3-morpholinone (III) and 5-chlorothiophene-2-carbonyl chloride (IV):

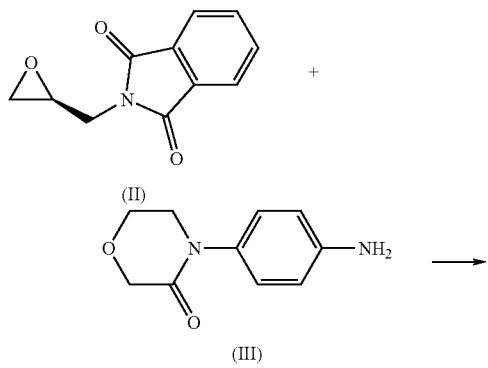

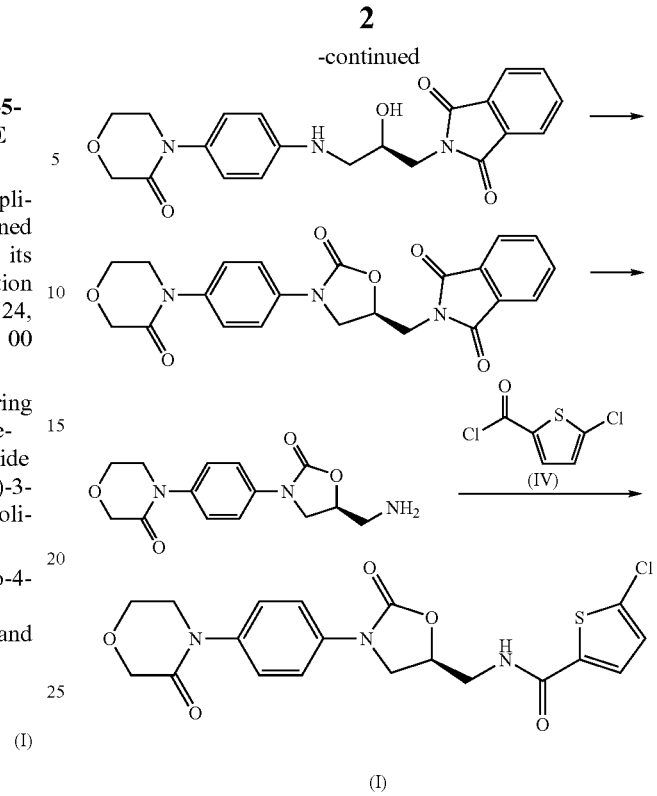

In this method, the epoxyphthalimide (II) is prepared by reacting (2S)-1-chloropropane-2,3-diol (V) with potassium carbonate via the stage of (S)-glycidol (VI) and subsequent Mitsunobu reaction with phthalimide:

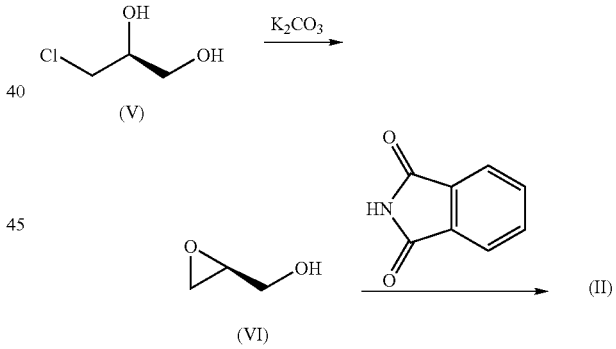

The process known from WO-A 01/47919 has various disadvantages which have a particularly unfavorable effect when the compound of the formula (I) is prepared on the industrial scale:

For instance, the glycidol (VI), especially in relatively large amounts, is polymerization-sensitive and thus not storage-stable, additionally toxic and potentially carcinogenic. The Mitsunobu reaction in the preparation of compound (II) is technically costly and inconvenient, one reason being that racemization occurs readily in relatively large batches. Another reason is that the atom economy is extremely unsatisfactory, since triphenylphosphine oxide and diisopropyl azodicarboxylate hydrazide are generated in stoichiometric amounts as waste materials. In addition, the nitrogen atom in the oxazolidinone ring of the target molecule (I) is introduced in phthalimide-protected form. However, the phthalic acid radical as a protecting group has to be removed in the further course of the synthesis, which means an increase in the number of stages and additional waste.

It is thus an object of the present invention to provide a simplified process for preparing the compound of the formula (I) in large amounts.

It has been found that, surprisingly, the compound of the formula (I) can be prepared in improved yield in a shortened reaction sequence using storage-stable and less toxic starting materials, starting from 5-chlorothiophene-2-carbonyl chloride (IV), (2S)-3-aminopropane-1,2-diol hydrochloride (VII) and 4-(4-aminophenyl)-3-morpholinone (III), In this reaction sequence, the use of protecting groups is also avoided, which reduces the number of stages and thus shortens the reaction time.

In the first step of the process according to the invention, 5-chlorothiophene-2-carbonyl chloride (IV)

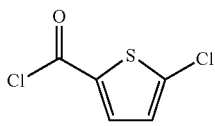

(IV)

is prepared from 5-chlorothiophene-2-carboxylic acid.

Compound (IV) may be prepared under the customary reaction conditions for the preparation of carbonyl chlorides from the corresponding carboxylic acids. Preference is given to the reaction of 5-chlorothiophene-2-carboxylic acid with thionyl chloride as the chlorinating reagent in toluene as the solvent.

In the second step of the process according to the invention, 5-chlorothiophene-2-carbonyl chloride (IV) is reacted with (2S)-3-aminopropane-1,2-diol hydrochloride (VII)

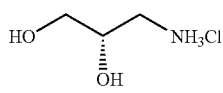

(VII)

to give N-((S)-2,3-dihydroxypropyl)-5-chlorothiophene-2-carboxamide (VIII)

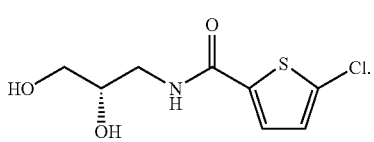

(VIII)

The reaction (IV)+(VII)->(VIII) may be effected under the reaction conditions customary for the formation of amide bonds from the appropriate carbonyl chlorides and amines. Preference is given to a biphasic system composed of aqueous sodium hydrogencarbonate solution and 2-methyltetrahydrofuran as the organic solvent. (2S)-3-Aminopropane-1,2-diol is used in the form of the free base or in the form of the acid addition salt. Preference is given to the hydrochloride (VII) which crystallizes better than the free base and can therefore be handled readily. To increase the reaction yield, optionally either an excess of amine is used or an auxiliary base is added. The addition of from 1 to 3, preferably 2, equivalents of an auxiliary base such as sodium hydrogencarbonate is preferred. The reaction is effected generally within a temperature range of from 0° C. to 40° C., preferably of from 5° C. to 30° C.

In the third step of the process according to the invention, N-((S)-2,3-dihydroxypropyl)-5-chlorothiophene-2-carboxamide (VIII) is converted to N-((S)-3-bromo-2-hydroxypropyl)-5-chlorothiophene-2-carboxamide (IX)

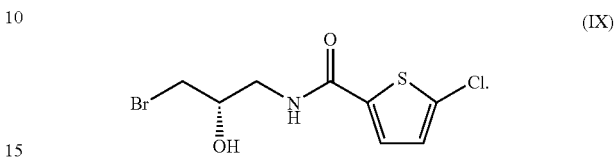

(IX)

The reaction (VIII)->(IX) is carried out with from 1 to 5, preferably from 3 to 5, in particular 4, equivalents of a solution of hydrobromic acid in acetic acid, optionally in the presence of acetic anhydride. The reaction temperature is between 20° C. and 80° C., preferably between 60 and 65° C. The amount of methanol added may be varied over a wide range; preference is given to using from 40 to 80 mol, in particular from 50 to 60 mol, of methanol per mole of (VIII). For the workup, the solvents are distilled off, preferably under reduced pressure. The remaining distillation residue is optionally also neutralized before the filtration of the product.

In the fourth step of the process according to the invention, N-((S)-3-bromo-2-hydroxypropyl)-5-chlorothiophene-2-carboxamide (IX) is reacted with 4-(4-aminophenyl)-3-morpholinone (III)

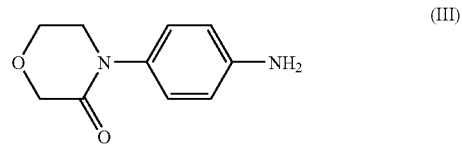

(III)

to give N-{(R)-2-hydroxy-3-[4-(3-oxomorpholin-4-yl)-phenylamino]propyl}-5-chlorothiophene-2-carboxamide (X)

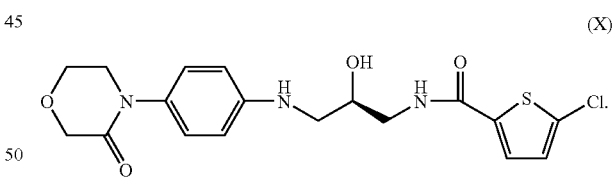

(X)

The solvent for the reaction (IX)+(III)->(X) may be varied widely; preference is given to toluene. The reaction temperature is between 80° C. and 200° C.; preference is given to a range between 90° C. and 110° C. The reaction is effected optionally in the presence of an auxiliary base, for example triethylamine, diisopropylethylamine or collidine; preference is given to using collidine. The stoichiometry of the reaction and the reaction time are variable over a wide range; preference is given to a ratio of compound (IX) to compound (III) to collidine of 1.2 to 1.0 to 1.0 and a reaction time of from 4 to 8 hours, especially of from 5 to 6 hours.

In the fifth step of the process according to the invention, N-{(R)-2-hydroxy-3-[4-(3-oxomorpholin-4-yl) phenylamino}propyl]-5-chlorothiophene-2-carboxamide (X) is reacted with phosgene or a phosgene equivalent to give 5-chloro-N-({(5S)-2-oxo-3-[4-(3-oxo-4-morpholinyl)phenyl]-1,3-oxazolidin-5-yl}methyl)-2-thiophene-carboxamide (I).

In the reaction (X)->(I), one or more equivalents of phosgene or phosgene equivalents are used in the presence of inert solvents or solvent mixtures. Phosgene equivalents are, for example, phosgene replacements such as di- or triphosgene, or carbon monoxide equivalents, for example N,N-carbonylbisimidazole. Preference is given to using from 1 to 2 equivalents, in particular from 1.1 to 1.3 equivalents, of N,N-carbonylbisimidazole in a solvent mixture of 1-methyl-2-pyrrolidone and toluene. For purification of the product, a clarifying filtration and/or a recrystallization optionally follows. The reaction is effected generally within a temperature range of from 20° C. to 150° C., preferably of from 30° C. to 110° C., in particular of from 75° C. to 85° C.

The individual stages of the process according to the invention may be carried out at standard, elevated or at reduced pressure (for example of from 0.5 to 5 bar). In general, standard pressure is used.

The following scheme summarizes the synthesis:

from 40 to 48 mbar. The thus obtained solution of the acid chloride in toluene is reacted directly in the next stage.

2nd Step:

N-((S)-2,3-Dihydroxypropyl)-5-chlorothiophene-2-carboxamide (VIII)

461 g of sodium hydrogencarbonate and 350 g of (2S)-3-aminopropane-1,2-diol hydrochloride (VII) (commercially available) are initially charged at from 13 to 15° C. in 2.1 l of water and admixed with 950 ml of 2-methyltetrahydrofuran. 535.3 g of 5-chlorothiophene-2-carbonyl chloride (approx. 93%) in 180 ml of toluene are added dropwise to this mixture with cooling at from 15 to 18° C. over a period of two hours. For workup, the phases are separated and the organic phase is admixed in several steps with a total of 1.5 l of toluene. The precipitated product is filtered off with suction, washed with ethyl acetate and dried.

Yield: 593.8 g; corresponds to 91.8% of theory.
Melting point: 114 to 114.5° C.

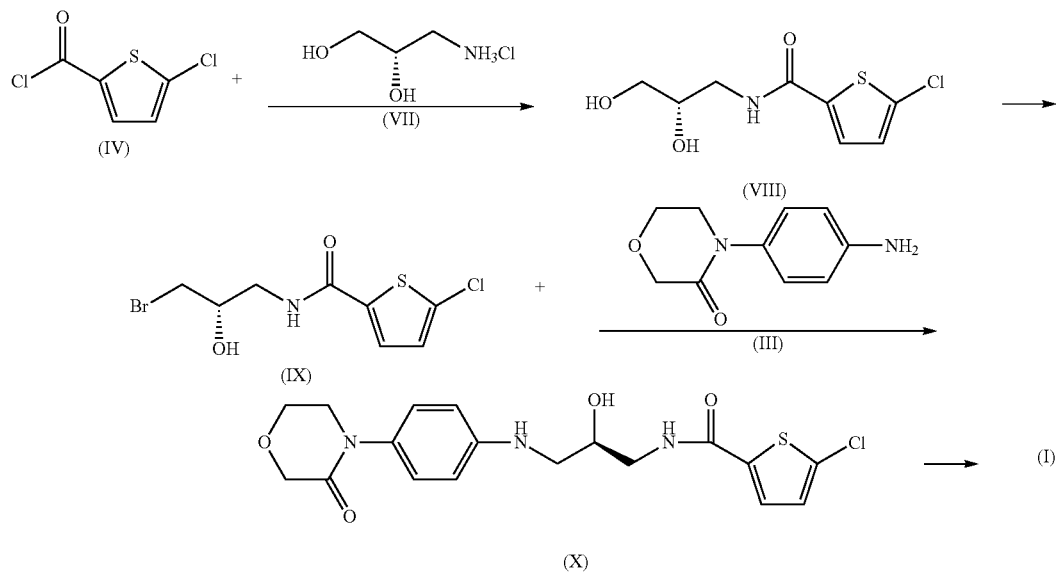

The invention is illustrated in detail below by a preferred working example, to which it is not, however, restricted. Unless stated otherwise, all quantitative data relates to percentages by weight.

Synthesis of 5-chloro-N-({(5S)-2-oxo-3-[4-(3-oxo-4-morpholinyl)phenyl]-1,3-oxazolidin-5-yl}methyl)-2-thiophenecarboxamide (I)

1st Step:

5-Chlorothiophene-2-carbonyl chloride (IV)

53.6 g of 5-chlorothiophene-2-carboxylic acid (commercially available) are suspended in 344 g of toluene and heated to 80° C. At this temperature, 47.2 g of thionyl chloride are added dropwise over a period of 20 minutes, then the mixture is stirred at from 75 to 80° C. for 30 minutes and then at reflux temperature for two hours until completion of gas evolution. After cooling, the reaction mixture is concentrated to a volume of approx. 200 ml at from 30 to 35° C. and a pressure of 3rd Step:

N-((S)-3-Bromo-2-hydroxypropyl)-5-chlorothiophene-2-carboxamide (IX)

301.7 ml of a 33% solution of hydrobromic acid in acetic acid are added to a suspension of 100 g of N-((S)-2,3-dihydroxypropyl)-5-chlorothiophene-2-carboxamide (VIII) in 250 ml of glacial acetic acid at from 21 to 26° C. over a period of 30 minutes. Subsequently, 40 ml of acetic anhydride are added and the reaction mixture is stirred at from 60 to 65° C. for three hours. At 20 to 25° C., 960 ml of methanol are then added over a period of 30 minutes. The reaction mixture is stirred under reflux for 2.5 hours and then overnight at from 20 to 25° C. For workup, the solvents are distilled off under reduced pressure at approx. 95 mbar. The remaining suspension is admixed with 50 ml of 1-butanol and 350 ml of water. The precipitated product is filtered off with suction, washed with water and dried.

Yield: 89.8 g; corresponds to 70.9% of theory.
Melting point: 120° C.

4th Step:

N-{(R)-2-Hydroxy-3-[4-(3-oxomorpholin-4-yl)phenylamino]propyl}-5-chloro-thiophene-2-carboxamide (X)

55 g of N-((S)-3-bromo-2-hydroxypropyl)-5-chlorothiophene-2-carboxamide (IX) and 29.4 g of 4-(4-aminophenyl)-3-morpholinone (III) (a preparation method is described, for example, in WO-A 01/47919 on pages 55 to 57) are suspended at from 20 to 25° C. in 500 ml of toluene and admixed with 18.5 g of collidine and 10 ml of ethanol. The reaction mixture is heated to from 103 to 105° C. for 6 hours and then admixed while hot with 50 ml of 1-butanol. After cooling to 30° C., the precipitated reaction product is filtered off with suction, washed with toluene and water and dried.

Yield: 42.0 g; corresponds to 61.8% of theory.
Melting point: 198.5° C.

5th Step:

5-Chloro-N-({(5S)-2-oxo-3-[4-(3-oxo-4-morpholinyl)phenyl]-1,3-oxazolidin-5-yl}methyl)-2-thiophenecarboxamide (I)

25 g of N-{(R)-2-hydroxy-3-[4-(3-oxomorpholin-4-yl)phenylamino]propyl}-5-chlorothiophene-2-carboxamide (X) are suspended at from 20 to 25° C. in 250 ml of toluene and admixed with 37.5 ml of 1-methyl-2-pyrrolidone and 11.9 g of N,N-carbonyldiimidazole. The reaction mixture is heated to from 80 to 83° C. for 20 minutes and subsequently heated to 115° C. for one hour. After cooling to 20° C., the precipitated reaction product is filtered off with suction, washed twice with 25 ml each time of water and dried at 60° C. under reduced pressure.

Yield; 23.7 g; corresponds to 91.5% of theory.
Melting point: 230° C.

What is claimed is:

1. A process for preparing 5-chloro-N-({(5S)-2-oxo-3-[4-(3-oxo-4-morpholinyl)phenyl]-1,3-oxazolidin-5-yl}methyl)-2-thiophenecarboxamide of the formula (I)

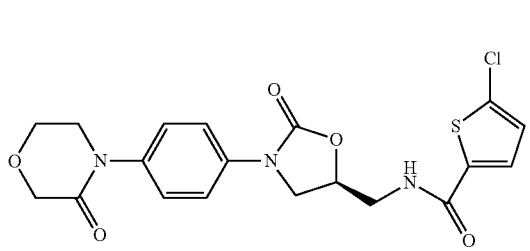

comprising preparing 5-chlorothiophene-2-carbonyl chloride (IV) in a first step by chlorinating 5-chlorothiophene-2-carboxylic acid;
reacting said 5-chlorothiophene-2-carbonyl chloride (IV) in a second step with (2S)-3-aminopropane-1,2-diol hydrochloride (VII) to give N-((S)-2,3-dihydroxypropyl)-5-chlorothiophene-2-carboxamide (VIII);
converting said N-((S)-2,3-dihydroxypropyl)-5-chlorothiophene-2-carboxamide (VIII) in a third step to N-((S)-3-bromo-2-hydroxypropyl)-5-chlorothiophene-2-carboxamide (IX);
converting said N-((S)-3-bromo-2-hydroxypropyl)-5-chlorothiophene-2-carboxamide (IX) in a fourth step by reacting with 4-(4-aminophenyl)-3-morpholinone (III) to N-{(R)-2-hydroxy-3-[4-(3-oxomorpholin-4-yl)phenylamino]propyl}-5-chlorothiophene-2-carboxamide (X); and
reacting said N-{(R)-2-hydroxy-3-[4-(3-oxomorpholin-4-yl)phenylamino]propyl}-5-chlorothiophene-2-carboxamide (X) in a fifth step with phosgene or a phosgene equivalent.

2. A process for preparing N-{(R)-2-hydroxy-3-[4-(3-oxomorpholin-4-yl)phenylamino]propyl}-5-chlorothiophene-2-carboxamide (X), comprising reacting N-((S)-3-bromo-2-hydroxypropyl)-5-chlorothiophene-2-carboxamide (IX) with 4-(4-aminophenyl)-3-morpholinone (III).

3. A process for preparing 5-chloro-N-({(5S)-2-oxo-3-[4-(3-oxo-4-morpholinyl)phenyl]-1,3-oxazolidin-5-yl}methyl)-2-thiophenecarboxamide of the formula (I), comprising reacting N-{(R)-2-hydroxy-3-[4-(3-oxomorpholin-4-yl)phenylamino]propyl}-5-chlorothiophene-2-carboxamide (X) with phosgene or a phosgene equivalent and further comprising preparing said N-{(R)-2-hydroxy-3-[4-(3-oxomorpholin-4-yl)phenylamino]propyl}-5-chlorothiophene-2-carboxamide (X) by reacting N-((S)-3-bromo-2-hydroxypropyl)-5-chlorothiophene-2-carboxamide (IX) with 4-(4-aminophenyl)-3-moxpholinone (III).

4. The process as claimed in claim 3, characterized in that the phosgene equivalent is N,N-carbonyldiimidazole.

5. The process as claimed in claim 4, characterized in that from 1.1 to 1.3 equivalents of N,N-carbonyldiimidazole are used.

6. The process of claim 3, wherein the reaction takes place in a solvent mixture of 1-methyl-2-pyrrolidone and toluene.

7. The process of claim 3, further comprising preparing the N-((S)-3-bromo-2-hydroxypropyl)-5-chlorothiophene-2-carboxamide (IX) by reacting N-((S)-2,3-dihydroxypropyl)-5-chlorothiophene-2-carboxamide (VIII) with hydrobromic acid in acetic acid.

8. The process of claim 7, further comprising preparing said N-((S)-2,3-dihydroxypropyl)-5-chlorothiophene-2-carboxamide (VIII) by reacting 5-chlorothiophene-2-carbonyl chloride (IV) with (2S)-3-aminopropane-1,2-diol hydrochloride (VII).

9. N-((S)-3-Bromo-2-hydroxypropyl)-5-chlorothiophene-2-carboxamide of the formula (IX)

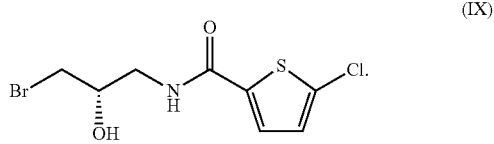

* * * * *